United States Patent
Wasser et al.

(12) 
(10) Patent No.: US 6,383,799 B1
(45) Date of Patent: May 7, 2002

(54) PROCESS FOR PRODUCING, METHODS AND COMPOSITIONS OF GLUCURONOXYLOMANNAN AS NUTRICEUTICAL AGENT FROM HIGHER BASIDIOMYCETES MUSHROOM

(75) Inventors: Solomon P. Wasser, Haifa (IL); Sergey V. Reshetnikov, Kiev (UA)

(73) Assignee: MedMyco Ltd., Haifa (IL)

(*) Notice: Subject to any disclaimer, the term of this patent is extended or adjusted under 35 U.S.C. 154(b) by 0 days.

(21) Appl. No.: 09/419,207

(22) Filed: Oct. 15, 1999

(51) Int. Cl.$^7$ .............................. C12N 1/14; C12N 1/16; C12N 1/18
(52) U.S. Cl. ........................................ 435/254.1; 47/1.1
(58) Field of Search .......................... 47/1; 71/5; 426/7; 800/297; 260/112.5; 424/115, 116, 123; 435/254.1, 244

(56) References Cited

U.S. PATENT DOCUMENTS

| | | | | |
|---|---|---|---|---|
| 4,159,225 A | | 6/1979 | Yoshikumi et al. ............ 195/31 |
| 4,369,253 A | * | 1/1983 | Takita et al. ................. 435/244 |
| 5,334,704 A | | 8/1994 | Tsunoo et al. ............... 530/371 |
| 6,120,772 A | | 9/2000 | Ito et al. .................... 424/195.1 |

FOREIGN PATENT DOCUMENTS

| | | |
|---|---|---|
| CN | 1125065 | 6/1966 |
| CN | 1044036 | 7/1990 |
| CN | 1057954 | 1/1992 |
| CN | 1066964 | 12/1992 |
| CN | 1069866 | 3/1993 |
| CN | 1072829 | 6/1993 |
| CN | 1082362 | 2/1994 |
| CN | 1091263 | 8/1994 |
| CN | 1099946 | 3/1995 |
| CN | 1109300 | 10/1995 |
| CN | 1114871 | 1/1996 |
| CN | 11781222 | 4/1998 |
| CN | 1204474 | 1/1999 |
| JP | 6153879 | 6/1994 |
| JP | 7238031 A | 9/1995 |

OTHER PUBLICATIONS

Agric Biol. Chem. 1979, 43(8):Abstract.
Drug Dev. Res. 1989 17(2): Abstract.
China J. Antibiot. 1985, 10(6): Abstract.
Yakugaku–Zasshi, 1994, 114(5): Abstract.
Int. J. Medicinal Mushrooms, 1999, 1:139–146.
Mushroom Science, 1989, 12: 631–643.
Int. J. Medicinal Mushrooms 1999, 1, 1–7.
Int. J. Medicinal Mushrooms 1999, 9–29.
Nutriter Res. 1996, 16: Abstract.

* cited by examiner

*Primary Examiner*—Bruce R. Campell
*Assistant Examiner*—Kent L. Bell
(74) *Attorney, Agent, or Firm*—Rashida A. Karmali

(57) ABSTRACT

The present invention describes new and distinct strains of higher Basidiomycetes mushrooms grown in submerged cultures. Specifically, the new strain of species of the genus Tremella offer superior yields of one-cell biomass and exocellular heteropolysaccharide glucuronoxylomannan, niacin and essential amino acids.

2 Claims, 5 Drawing Sheets

PROCESS FOR PRODUCING, METHODS AND COMPOSITIONS OF GLUCURONOXYLOMANNAN AS NUTRICEUTICAL AGENT FROM HIGHER BASIDIOMYCETES MUSHROOM

FIELD OF THE INVENTION

The present invention is directed to a process for culturing a variety of higher Basidiomycetes mushrooms using defined media, to produce superior yields of biologically active nutriceuticals. The nutriceutical agents are isolated by a simple one-step process, and are formulated for use as dietary supplements to achieve normal human bodily functions in general, and to control hyperglycemia in particular. Specifically, this invention relates to a method of producing a polysaccharide glucuronoxylomannan, which has medicinal properties, and a biomass rich in the essential amino acids and vitamins, from the culture broth obtained from a submerged culture of an edible higher Basidiomycetes mushroom belonging to the genus Tremella.

1. BACKGROUND OF THE INVENTION

Mushrooms or macrofungi with distinctive fruiting bodies of sufficient size to be seen with the naked eye, include about 10,000 species of varying degrees of edibility. Approximately 100 species have been tested for cultivation and only seven to eight have been cultivated on an industrial scale. The world production of cultivated edible mushrooms in 1994 was estimated to be about five million tons and was valued at about ten billion US dollars. The most popular species of cultivated edible mushrooms include *Agaricus bisporus* (J. Lge) Imbach, *A. bitorquis* (Quél.) Sacc., *Lentinus edodes* (Berk) Sing., Pleurotus spp., Auricularia spp., *Volvariella volvacea* (Fr.) Sing., *Flammulina velutipes* (Fr.) Sing., *Tremella fuciformis* Berk., *Hypsizygus marmoreus* (Peck) Bigel., *Pholita nameko* (T. Ito) S. Ito et Imai, *Grifola frondosa* (Dicks.: Fr.) S.F. Gray, *Hericium erinaceus* (Bull.: Fr.) Pers., *Dictyophora indusiata* (Vent.: Pers.) Fischer, *Stropharia rugosoannulata* Far. apud Murr., *Lepista nuda* (Bull.: Fr.) Cooke, *Agrocybe aegerita* (Brig) Sing.

The cultivation of fruiting bodies of mushrooms deals with living organisms, for example, the mushroom itself and other microorganisms which may either be harmful or beneficial. Therefore, the methods employed in mushroom cultivation require modifications depending upon the region being cultivated, substrates available, environmental conditions and species of microorganisms encountered.

The cultivation of mushrooms for fruit bodies production is a long-term process needing from one to several months for the first fruiting bodies to appear. Moreover, it was found that processes for extraction of polysaccharides from fruit bodies are not considered commercially feasible, since the physicochemical properties of the products resulting from these processes were not known or regulated, Otsuka, U.S. Pat. No. 4,051,314. Submerged culturing of polysaccharide producers allows obtaining the end product of constant composition in a short period under controlled conditions using ecologically pure culture medium of defined composition.

Several species of the genus Tremella have been used in folk medicine since ancient times. These are *T. fuciformis, T. mesenterica, T. aurantia,* and *T. cinnabarina*, and all of them are characterized as "strengthening health, resisting disease," Yang Q. et al, 1989, Mushroom Science 12: 631–643. The last three species, with yellow-gold fruit bodies, are known under the common name "Kinji" in Oriental medicine and are considered to possess equal medicinal value, Ukai S. et al., 1995, JP 7, 238, 031 A.

Tremella mushrooms belong to the so-called jelly mushrooms, which form gelatinous fruit bodies. The jelly mushrooms are a set of species from different taxonomical groups of Phragmobasidiomycetes, which are able to survive long periods of drought by drying to a horny texture. When moisture is again available, they absorb water and become gelatinous. This characteristic of jelly mushrooms is due to the presence of specific water absorbing polysaccharides that compose 60–70% of the dry fruiting body. Unlike the β-1-3-glucans polysaccharides from other medicinal mushrooms, jelly mushroom polysaccharides consist of other sugars as well as glucose, and therefore belong to the class of heteropolysaccharides. A unique feature of Tremella mushrooms is that their pharmacologically active polysaccharides make up most of the structural fruit body polysaccharides while in other medicinal mushrooms pharmacologically active polysaccharides make up only a small part of the biomass. For example, in shiitake mushrooms only 31 g of lentinan was extracted from 200 kg of fresh mushrooms, Mizuno, 1999, Int. J. Medicinal Mushrooms, 1:7–27.

The main pharmacologically active substance from Tremella is the polysaccharide glucuronoxylomannan, consisting of a linear backbone of 1,3-linked alpha-D-mannose with mainly xylose and glucuronic acid in side chains. The chemical structure of Tremella glucuronoxylomannan differs among various samples of even one species, and may be in some way connected with a type of polysaccharide-based method of identification. The general proportions of xylose:glucuronic acid:mannose are given in *Tremella fuciformis* as 1.0:2.77:4.9; 2:1:4 in *T. aurantia*, and 7:1:5 in *T. mesenterica*, Fraser CE et al., 1973, Can J. Biochem. 51: 219–224. Some additional saccharides can be identified in different samples of *T. fuciformis*, such as glucose and fucose, xylobiose and fructose.

Several species of Tremella produce glucuronoxylomannan which has been shown to have hypocholesterolemic activity. Hypercholesterolemia and dyslipoproteinemia, causing high blood pressure and diabetes, are the main risk factors determining ischemic cardiopathologies and cerebral vascular accidents. Hypercholesterolemia is defined as the increase of the blood cholesterol ratio above 2 g/l. Dyslipoproteinemia coincides with the disturbance of diverse lipoprotein levels, resulting in lipid sedimentation on the arterial walls. *Tremella fuciformis* fruiting bodies, taken as 5% dried powder in a hypercholesterolemic diet (1.5% cholesterol, 5% fat), decreased the serum total cholesterol concentration in rats 19% after 4wk of mushroom diet consumption. Similar significant decreases in serum low-density lipoprotein (LDL) and triacylglycerol levels were observed, Cheung, PCK, 1996, Nutrition Res. 16: 1721–1725.

The antilipemic effect of polysaccharides from both *T. fuciformis* fruit body and pure culture has been described earlier, Janhe S. et al., 1989, J. China Pharm. Univ., 20:344–347, and it has been proposed that Tremella polysaccharides may be useful as dietary supplement in the prevention and therapy of atherosclerosis, Ryong LH et al., 1989, Drug Dev. Res. 17: 109–117. In addition, Tremella polysaccharides may have hepatoprotective functions in cases of chronic hepatitis Xiong HZ et al., 1985, Chin. J. Antibiot. 10: 363–365.

*Tremella aurantia* was found to have hypoglycemic activity in normal mice and in two diabetic mouse models, streptozotocin-induced diabetes and genetic diabetes. Diabetes is defined by a fasting glycemia above 1.4 g/l evaluated on two different blood samples. Insulin-dependent diabetes (IDD) corresponds to a fault in insulin secretion; cardiovascular complications are due to the important and lasting hyperglycemia causing the persistence of proteins in the urine. *Tremella aurantia* fruit body polysaccharide (TAP) was found to be effective in reducing hyperglycemia following not only intraperitoneal, but also oral administration (0.5 g/l TAP). Similar effects in prevention and treatment of alloxan- or streptozotocin-induced diabetic mice were shown for *T. fuciformis* polysaccharides, Xue W. et al, 1989, J. China Pharm. Univ. 20: 181–183; It was proposed that the mechanism of hypoglycemic activity in normal mice was at least related the increase of insulin secretion and for the acceleration of glucose metabolism Kiho, T. et al., 1994, Yakugaku-Zasshi,114:308–315.

Acid heteroglycans from *T. fuciformis* was found to have cytokine-stimulating activity. Four kinds of acidic heteroglycans with molecular weights from 550 to 48 KDa were isolated from the fruit bodies. These and additional fragments of their acidic hydrolysate also induced monocytes to secrete interleukin-6 with high potency, indicating that the activity may be caused by a common structure, $(1\rightarrow 3)$-mannan in the four heteroglycans and their fragments. So, the change of molecular weight had no obvious influence on the activity of the heteroglycans, Gao Q. et al., 1996, Carbon Res. 288:135–142.

Naturally growing or artificially cultivated fruit bodies of Tremella mushrooms have been extensively used during the last decade for development of different types of Tremella health-care nutritive or medicinal food, drink or beverage (CN Patt. 1125065; 1109300; 1102305; 1099946; 1091263; 1082362; 1072829; 1066964; 1044036; 1204474; 1178122; 1114871; JP Pat. 6153879; 6339354; 60075279).

These Tremella-by products can be classified as "mushroom nutriceuticals", which are refined/partially defined extracts from either the mycelium or the fruiting body of the mushroom, which are consumed in the form of capsules or tablets as a dietary supplement or functional foods, and which have potential therapeutic applications. Chang ST, 1999, Int. J. of Medicinal Mushrooms 1: 1–7. In this way nutriceuticals differ from "nutraceuticals" which are consumed as part of the normal diet and may have been modified/enriched in some way to provide health-giving benefits. Enriched compositions of nutriceuticals may thus be prepared by selecting the appropriate strains of mushroom and/or by optimizing the culture cultivation conditions. Hence the regulatory requirements for approval of nutriceuticals for human consumption may be more stringent than those for nutraceuticals.

However, it is found that nutraceutical products from fruiting bodies of medicinal mushrooms are very diverse in quality and quantity of different nutrients, and there are heretofore, no standard protocols for guaranteeing reproducible high product quality. Chang ST et al, 1999, Int. J. of Medicinal Mushrooms 1: 139–146. So, it is generally desirable to have nutriceutical compositions that are relatively uniform as to the type and levels of nutrients present in them. Generally, it has been found in cultivating different mushroom strains, that the polysaccharides extracted from the fruit bodies and from mycelia in pure cultures are not essentially the same, although both may be pharmacologically active. A slight difference was observed in xylose:glucuronic acid:mannose proportions in *Tremella fuciformis* polysaccharide from fruit bodies (1.0:2.77:4.9) and those obtained from pure cultures of different haploid yeast-like budding strains—1:0.8–1.3:2.1–3.5, Kakuta M. et al., 1979, Agric. Biol. Chem. 43: 1659–1668. The *Tremella fuciformis* polysaccharide had a hypocholesterolemic effect, which is characteristic for fruit bodies polysaccharide, when tested in rats with the addition of submerged culture-derived polysaccharide to a high-cholesterol diet.

Alternatively, acidic technology has been proposed to produce Tremella proteoglycan from artificially growing mycelium on a semisolid medium after fruit bodies have been removed from this substrate (CN Pat. 1071060). A pure culture of Tremella was used for production of a fermented beverage, when Tremella strains were inoculated in a liquid medium made with potato as the main raw material. The fermented liquor was directly made into a Tremella polysaccharide beverage after filtration and also could be concentrated and dried in order to obtain crude Tremella polysaccharide powder (CN Pat. 1069866; 1057954). This high-level nutritive beverage which fully embodies the nutritive and medicinal value of Tremella is proposed for enhancing the effect on human immunity and exerting antiageing, anti-tumor, or anti-hyperlipemia effects.

A special method for increasing the growth rate of Basidiomycetes species *Coriolus versicolor* pure culture was developed (U.S. Pat. No. 4,159,225). It was found that when dycariotic mycelium of this species was subjected to submerged culture while undergoing a mechanical treatment such as grinding or shearing in a liquid medium, the mycelium lost clamp connection, which is an intrinsic morphological characteristic, and changed into a monocariotic mycelium, and that the thus-formed monocariotic mycelium was stable and also had a unique characteristic in its extremely high propagation rate as compared with the known dycariotic mycelium.

A unique feature of some Heterobasidiomycetes species, to which the Tremella species belongs, is that their monocariotic (haploid) strains are able to grow in the form of yeast-like budding cells, and these monocariotic strains can be obtained not by grinding dycariotic mycelium but by development of monobasidiosporous cultures from the basidiospore print. This biological phenomenon was used for the production of *Tremella fuciformis* food and beverage, when yeast-like cells obtained by cultivating T-9 haploid strain (FERM No. 9419) in a submerged culture were blended with other components to form a food and beverage having an inhibitory action on a rise in cholesterol (JP Pat. 1020070). Heretofore, one cell cultures of Tremella have not been used to produce compounds having a hypoglycemic activity, and in particular, one cell cultures of *Tremella mesenterica* have not been used for any purpose.

2. SUMMARY OF THE INVENTION

The present invention relates to cultivation in submerged culture containing defined nutrient medium, of a one cell culture of the edible Basidiomycetes mushrooms comprising the genus Tremella including, but not limited to *Tremella mesenterica, T. fuciformis, T. aurantia*, and *T. encepuala*.

In a first aspect, the invention provides a method of cultivating submerged cultures of one or more Basidiomycetes mushrooms having the trait to produce one or more substances having hypoglycemic activity. The use of the nutrient media of the invention, comprising a saccharide containing glucose in the molecule, an organic or mineral source of nitrogen and a variety of salts, is especially suited to enhance the production of glucuronoxylomannan, having a hypoglycemic activity, by submerged culturing of haploid yeast-like budding cultures of an edible mushroom selected from *Tremella mesenterica*.

In the second aspect, the invention provides a method to concentrate the hypoglycemic compound together with mushroom cells thus enabling the simple separation of the edible one-cell biomass and exocellular polysaccharides from the fermentation broth by alcohol precipitation, thereby requiring no further extraction, concentration, purification or complex separation procedures. The simple separation of the edible Basidiomycetes from the culture broth of the present invention is followed by drying after extraction with alcohol.

In accordance with the invention, compositions including glucuronoxylomannan, a glucose lowering compound is described, which, when orally consumed or ingested, lowers the blood levels of glucose. The preventive and/or treatment method of the invention therefore involves reduction of risk posed by elevated glucose in subjects at high risk of having diabetes.

The present invention can provide methods and compositions including nutriceutical components generally beneficial for promoting health, for example, glucuronoxylomannan, vitamins, protein rich in the essential amino acids and free amino acids.

Still other objects and advantages of the invention will in part be obvious and will in part be apparent from the specification.

DETAILED DESCRIPTION OF THE INVENTION

An object of the present invention was to overcome the deficiencies of the state of the art and to provide: i) a process for producing glucose-lowering compounds in an efficient and economic way, and ii) a nutriceutical composition that is edible and useful as a dietary supplement.

The strain of Tremella used in the present invention was obtained from the naturally growing fruit body collected in Israel on deciduous wood.

A basidiospore print was obtained from a fresh fruit body situated under a sterile Petri dish in a moist chamber with slowly decreasing humidity. The basidiospores were transferred into sterile water and spore suspension was spread on the surface of malt agar (Pronadisa, pH 6.5) in Petri dishes. The primary colonies appearing from individual basidiospores were transferred aseptically onto the slants of malt agar. Using the criteria specified for fruit bodies in the standard authority "Morphological and molecular studies in the genus Tremella", Chee-Jen Ch., published in 1998, Bibl. Mycologica, Band 174, and by comparison with known species, collected fruit body was determined as *Tremella mesenterica* Retz.: Fr.

In accordance with the Budapest Treaty on the international recognition of the deposit of microorganisms for purposes of patent procedure, one strain deposited as culture, showing the best yield of polysaccharide in preliminary tests, was deposited in the Centraalbureau voor Schimmelcultures (CBS), Oosterstraat 1. Postbus 273, NL 3740 AG Baarn. The Netherlands and was given Acc. No. CBS 101939.

| Species | Dep. No | Dep. Date |
|---|---|---|
| *Tremella mesenterica* Retz.: Fr. | CBS 101939 | June 14, 1999 |

Figure 1:
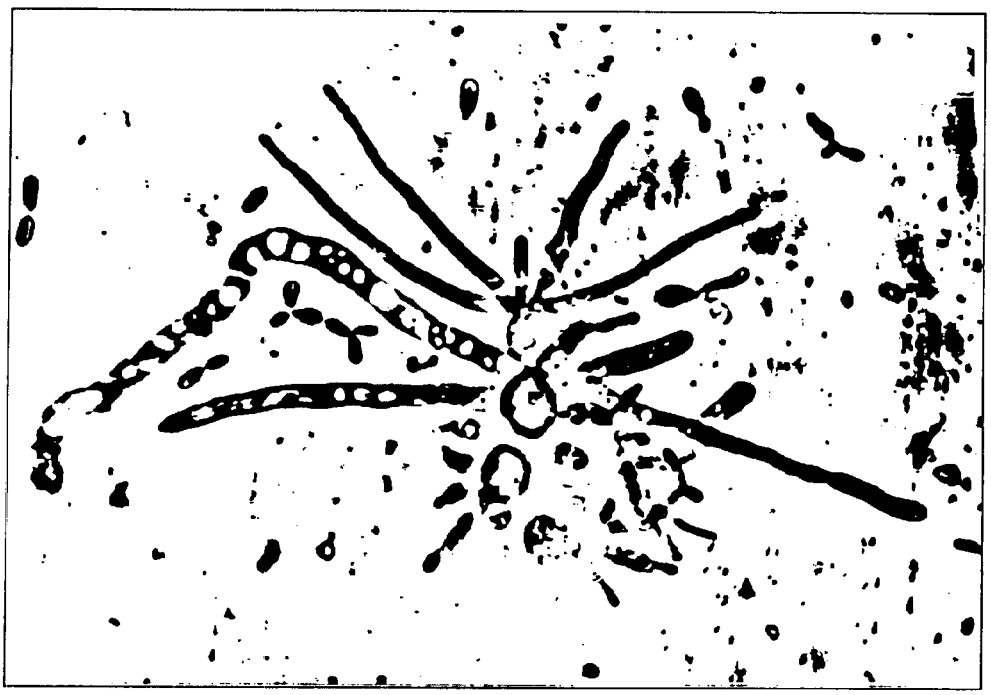
FIG. 1. Shows a view of germination of basidiospores, both by hyphae or budding cells. Objective x 100, phase contrast.
Figure 2:
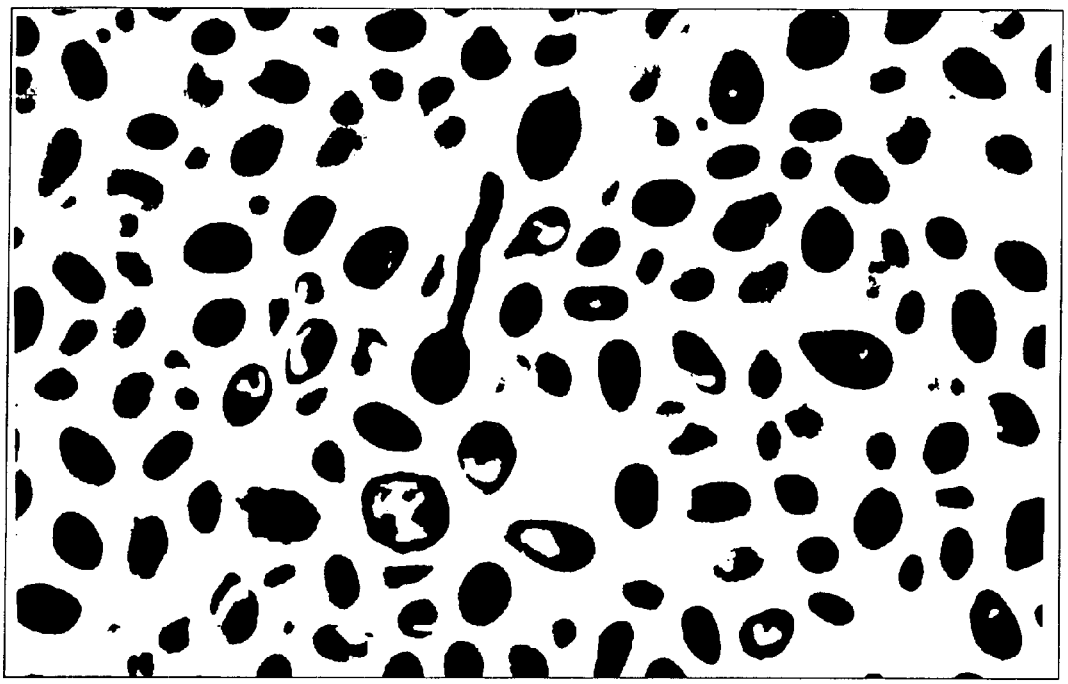
FIG. 2. Shows a view of cells of haploid strain; one cell is proliferating by haploid hypha. Objective x 100, phase contrast.
Figure 3:
FIG. 3. Shows a view of preparation of *Tremella mesenterica* in Indian ink. White area around cells indicates a polysaccharide slime envelope. It is well evident, that the polysaccharide matrix around yeast-like budding cells is much more voluminous that of the hypha. Objective x 100.
Figure 4:
FIG. 4. Shows a view of dycariotic mycelium with clamps originating from crossed compatible haploid strains. Haploid cells are visible in the field of view. Objective X40, phase contrast.
Figure 5:
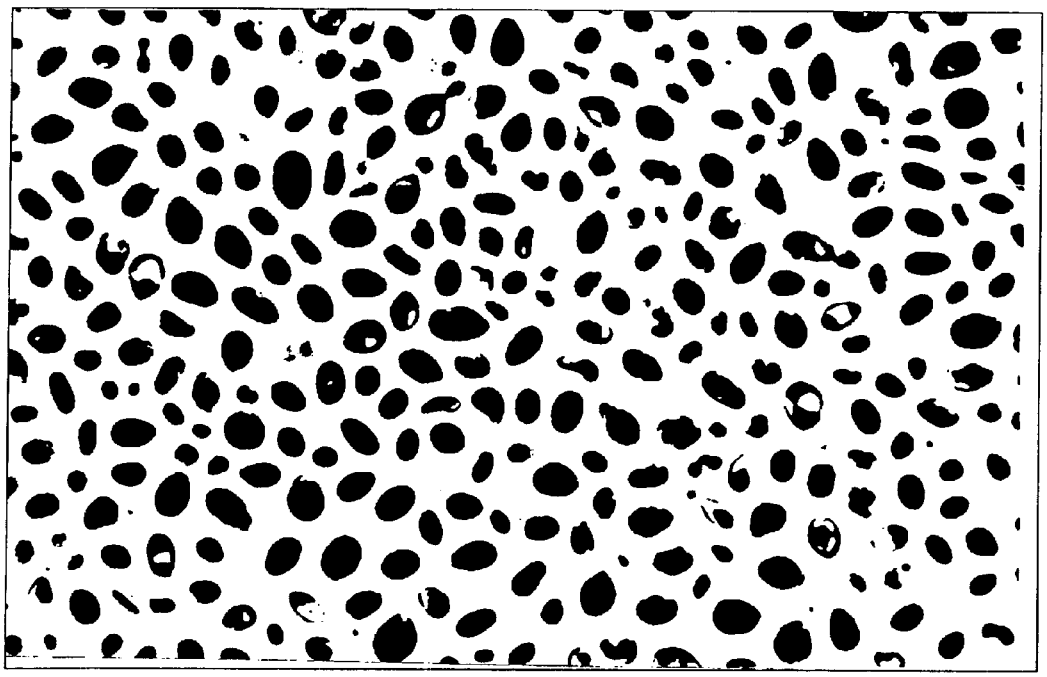
FIG. 5 shows a view of *Tremella mesenterica* CBS 101939 submerged culture. Objective x 100, phase.

*Tremella mesenterica* has a very complex life cycle. In contrast to other Basidiomycetes mushrooms a single basidiospore germinates on a nutrient medium broth by hypha and by yeast-like budding cells (FIG. 1). Monobasidiosporous culture is haploid, i.e. contains only one nucleus in each cell (FIG. 5). When two compatible haploid cells, originating from different basidiospores, come into contact, a plasmogamy and caryogamy occurs and dycariotic mycelium develops (FIG. 4). The dycariotic mycelium cannot grow in the form of budding cells, under any conditions of cultivation, so a yeast-like type of growth is genetically determined by a haploid status of mushroom culture. The haploid culture is more plastic, because on poor media or under conditions of exhaustion yeast-like cells can form haploid hypha (FIG. 2). One-cell fungi cultures, like other microorganisms, are more acceptable for biotechnological processes, than mycelial ones. This is especially important for Basidiomycetes dycariotic cultures, which grow in the form of sterile mycelium, and a special procedure for preparing Basidiomycetes inoculum is needed, that includes dycariotic mycelium homogenization. The haploid yeast-like budding culture of the present invention, is the most optimal form of growth not only from biotechnological considerations, but as defined by its physiological attribute of producing a larger amount of polysaccharide than mycelium form (FIG. 3).

In order to produce polysaccharide the culture of *T. mesenterica* CBS 101939 strain was carried out in aqueous media such as those employed for good growth and biomass accumulation. Such media contain sources of carbon, nitrogen and inorganic salts assimilated by the growing culture. *T. mesenterica* is capable of utilizing lignocellulose materials, so a wide range of carbohydrates including pentoses, hexoses and polysaccharides are good sources of carbon for their growth. Glucose, sucrose and starches such as grain, corn meal and the like are the main ingredients that can be used either alone or in combination as sources of carbon. The amount of carbohydrate usually varies between about 3% and 5% by weight of the medium to provide a high yield of biomass.

The best sources of nitrogen, usually in organic form, include yeast hydrolysates or extract, bacteriological peptone, corn steep liquor and the like. The sources of nitrogen either alone or in combination are used in the range of 0.5% to 4% by weight depending on N content in the source, but about 1 to 1.5 g of pure N per liter of culture medium.

Among inorganic salts, which can be incorporated in the culture media, are salts possessing cations of potassium, ammonium and magnesium. Sodium is not needed for growth at all. Useful cations can be obtained in the form of phosphate, or sulfate and chloride. The main microelements Fe, Mn, Zn and Cu are available from any type of inorganic salts.

The fermentation is carried out at temperatures ranging from 20° C. to 28° C. The optimal temperature for growth in a refrigerated orbital incubator is 27° C., and 28° C. is maximal; further increase of temperature is detrimental and at 30° C. *Tremella mesenterica* cells stopped their growth. The fermentation in submerged culture includes one stage of seed development. The liquid nutrient medium for the first step of inoculum preparation may be any suitable combination of carbon and nitrogen sources, preferably glucose or sucrose, and peptone or yeast extract. The seed flask inoculated from surface agar culture (tube or Petri dish) is filled with 100 ml of sterile medium and the seed flask is shaken 4–6 days at 100–120 rpm until growth is satisfactory. The seed flask is transferred to 1 liter of sterile medium, which may itself serve as inoculum in proportion 1 to 10 volumes.

The invention is not to be limited in scope by the embodiment disclosed in the examples which is intended as an illustration of one aspect of the invention and it is contemplated that the scope of the invention encompasses any number of species and genera of the Basidiomycetes mushrooms grown in submerged cultures in the form of yeast-like budding cells. It should include those that may be adjusted or modified, within the range of this invention, depending on its objective or usage.

EXAMPLE 1

A tube with a 6–8 days old pure culture of *Tremella mesenterica* CBS 101939 on malt agar pH 6.5 was used for inoculation into 100 ml of medium A in a 250 ml Erlenmeyer flask. The culture from the agar surface was washed off with sterile water. Medium A has the following composition (g/1):

| Medium A | |
| --- | --- |
| Glucose (Dextrose) - | 25 |
| Peptone - | 2 |
| Yeast extract - | 1 |
| $KH_2PO_4$ - | 0.5 |
| $MgSO_4.7H_2O$ - | 0.25 |
| $CaCl_2.2H_2O$ - | 0.1 |
| Corn Steep liquor - | 2.5 ml |
| Trace Element Mixture - | 10 ml |
| 10% KOH - | 2.5 ml |
| Trace Element Mixture (g/l): | |
| $FeSO_4.7H_2O$ - | 0.5 |
| $MnSO_4.H_2O$ - | 0.1 |
| $ZnSO_4.7H_2O$ - | 0.05 |
| $CuSO_4.5H_2O$ - | 0.02 |

After 30 min. of sterilization at 120° C., pH of the medium A is between 6.2 to 6.5.

The inoculated flasks were incubated in the refrigerated orbital incubator at 200 rpm, 27° C. After six days of growth the whole content of the seed flasks was transferred to inoculate 1000 ml of medium B in two-liter Erlenmeyer flasks and the fermentation process was carried out at 27° C. in the refrigerated orbital incubator at 200 rpm. Medium B has the following composition (g/l):

| Medium B | |
| --- | --- |
| Sucrose - | 30 |
| $NaNO_3$ - | 0.75 |
| $NaH_2PO_4\ H_2O$ - | 1.0 |
| KCl - | 1.0 |
| $MgSO_4.7H_2O$ - | 0.3 |

Before sterilization pH of the medium was adjusted to 6.5.

After 90 h of cultivation the culture broth was centrifuged at 4° C., 5000 rpm for 10 min. The biomass was determined in grams of dry weight after desiccation at 105° C. until constant weight was attained. Polysaccharide prediction was determined by the weight method from supernatant of centrifuged culture broth using ethanol for precipitation, 2–3 volumes to culture supernatant. After 24 h at 4° C. the precipitated crude biopolymer was separated by filtration and dried to constant weight.

The resulting crop of biomass on this fermentation medium B was 3.4 g/l and polysaccharide production after 90 h was 5.8 g/l.

EXAMPLE 2

A tube with a 6–8 days old pure culture of *Tremella mesenterica* CBS 101939 on malt agar pH 6.5 was used for inoculation of 100 ml of medium A in a 250 ml Erlenmeyer flask. The culture from the agar surface was washed off with sterile water. Before sterilization, pH of the medium was adjusted to 6.5. Medium A has the following composition (g/1):

| Medium A | |
| --- | --- |
| Sucrose - | 25 |
| Peptone - | 2.0 |
| Yeast extract - | 2.25 |
| $KH_2PO_4$ - | 1.0 |
| $MgSO_4.7H_2O$ | 0.5 |

The inoculated flasks were incubated in the refrigerated orbital incubator at 200 rpm, 27° C. After six days of growth the content of the seed flasks was transferred to inoculate 1000 ml of medium B in two-liter Erlenmeyer flasks and the fermentation process was carried out at 27° C. in the refrigerated orbital incubator at 200 rpm. Before sterilization, pH of the medium was adjusted to 6.5. Medium B has the following composition (g/1):

| Medium B | |
| --- | --- |
| Sucrose - | 40 |
| Peptone - | 1.0 |
| Yeast extract - | 1.1 |
| $NaHPO_4.7H_2O$ - | 1.0 |
| $NaH_2PO_4.7H_2O$ - | 0.5 |
| $KH_2PO_4$ - | 1.0 |
| Mg acetate - | 1.0 |
| KCl - | 1.0 |

After 5 days of cultivation 2 or 3 volumes of ethyl alcohol were added to culture broth. After 24 h at 4° C. the precipitated crude product was separated by filtration and dried to constant weight. The resulting product which consisted of both polysaccharide and one-cell biomass was 18.4 g/l. When measured independently according to the method described in example 1, polysaccharide yield was 13.9 g/l and biomass—7•7 g/l (some amount of polysaccharide is firmly attached with cells).

Amino acids analysis of obtained biomass showed that essential amino acids composed 31% of total amino acids content (Table 1). Thus, the nutriceutical composition of the present invention is a useful source to supply high quality protein rich in essential amino acids.

Table 1. The amino acid composition of the *Tremella mesenterica* CBS 101939 biomass.

TABLE 1

| Amino acids | Free | | Protein | |
|---|---|---|---|---|
| | µg/100 mg dry weight | %, dry weight | µg/100 mg dry weight | %, dry weight |
| Aspartic acid | 42.73 | 0.043 | 2252.27 | 2.652 |
| Threonine | 138.80 | 0.139 | 1700.96 | 1.700 |
| Serine | 204.87 | 0.205 | 2281.97 | 2.281 |
| Glutamatic acid | 557.08 | 0.557 | 2020.39 | 2.020 |
| Proline | — | | 1379.40 | 1.379 |
| Glycine | 162.11 | 0.162 | 1929.04 | 1.929 |
| Alanine | 604.10 | 0.604 | 2402.32 | 2.402 |
| Cysteine | — | — | 294.71 | 0.294 |
| Valine | 102.40 | 0.102 | 802.71 | 0.802 |
| Methionine | 210.40 | 0.210 | — | — |
| Isoleucine | 68.46 | 0.068 | 230.23 | 0.230 |
| Leucine | 153.80 | 0.0153 | 415.59 | 0.415 |
| Tyrosine | 83.58 | 0.083 | — | — |
| Phenylalanine | 71.35 | 0.071 | — | — |
| Histidine | 87.14 | 0.087 | 290.92 | 0.290 |
| Ornitine | 41.80 | 0.042 | 187.17 | 0.187 |
| Lysine | 47.87 | 0.047 | 1876.85 | 1.576 |
| Arginine | 88.04 | 0.088 | 528.82 | 0.528 |

Among vitamins of B group, determined by microbiological method, based on the estimation of growth characteristics of sensitive auxotroph microorganisms, *T. mesenterica* biomass is especially rich in niacin (Table 2). Thus, the nutraceutical composition of the present invention may be used as a vitamin supplement, in particular to supply a natural source of niacin.

Table 2 describes the group B vitamin content in *Tremella mesenterica* CBS 101939 biomass.

TABLE 2

| Vitamins | Content, pg/g dry weight |
|---|---|
| Thiamine, B1 | 1.58 +/− 0.05 |
| Niacin, B5 | 500.0 +/− 24 |
| Piridoxin, B6 | 1.0 +/− 0.01 |
| Biotine, B7 | 0.1 0.003 |

NUTRICEUTICAL FORMULATIONS AND METHOD OF USE

Nutriceutical compositions containing glucose-lowering compounds must be stable under the conditions of manufacture and storage and may be protected from contamination by microorganisms, such as fungi and bacteria, through the use of bacteriostatic agents, antioxidants such as vitamin E and ethoxyqiun, which are listed as generally safe for use by the Food and Drug Administration.

The formulation is taken as a single daily dose or divided daily doses, most preferably three doses given before, during or after meals. The formulation may be used in food or for garnishing and packaged accordingly. Patients can be maintained on glucose-lowering compounds indefinitely to regulate the blood glucose levels. Conditions to be considered in selecting dosage level, frequency, and duration, primarily include the severity of the patient's disorder, the patient's blood glucose level, adverse side effects and the patient's need for preventive intervention as well as the therapeutic efficacy. It is to be understood that for any particular subject, specific dosage regimens should be adjusted over time according to the individual patient need and the professional judgment of the person administering or supervising the administration of the nutriceutical compositions, and that the concentration ranges set forth herein are exemplary only and are not intended to limit the scope or practice of the claimed composition. Other concentration ranges and dosage durations can be determined by routine experimentation.

Diabetes mellitus is a disease of metabolic dysregulation, notably of glucose metabolism, and long-term vascular and neurologic complications. Diabetes has several clinical forms, the two major forms being insulin-dependent diabetes mellitus I (IDDM) and the non-insulin-dependent diabetes mellitus II (NIDDM). IDDM is rare, affecting one in 250 persons in the United States, where approximately 10,000 to 15,000 new cases are reported each year. Data suggest that the incidence of IDDM is increasing in Europe, where the highest prevalence is found in northern Europe, for example, more than one in every 150 Finns develop IDDM by 15 years of age. LaPorte, R. et al., in Diabetes in America, $2^{nd}$ ed. Ed M. Harris, National institutes of Health, Bethesda, Md. NIH Publication No 95-1498, 1995.

NIDDM is common, with an overall prevalence of 6.6 percent in the United States. NIDDM has become one of the most frequent chronic diseases in most industrialized nations and the projected prevalence for the next decade is 10 percent. 600,000 new cases are reported each year and one half of the NIDDM population are unaware of their disorder. The increase in the prevalence of NIDDM in the United States is commonly attributed to an aging population that is also increasingly obese and sedentary. The prevalence of NIDDM among persons older than 65 years exceeds 18 percent, and compared with normal-weight individuals, obese people with a body mass index greater than 30, are at 10 to 20 times greater risk for NIDDM. Although genetic and immunologic markers for IDDM have been identified, they are not enough nor sensitive enough to be used to define IDDM or distinguish IDDM and NIDDM. Harris, M. I., et al., Diabetes 36: 523 (1987); Bennett, P. H., et al., in International Textbook of Diabetes, ed Alberti KGMM, et al., John Wiley & Sons Ltd UK 1992, p148.

The natural hypoglycemic mushroom nutriceuticals are generally ingested orally. However, if individual agents are further extracted from the biomass, then the purified hypoglycemic agents may be administered intravenously, intraperitoneally, subcutaneously, intramuscularly, intrathecally, orally, rectally, topically, or by aerosol.

Formulations suitable for oral administration include liquid solutions of the active compound dissolved in diluents such as saline, water or PEG 400; capsules or tablets, each containing a predetermined amount of the active agent as solid, granules or gelatin; suspensions in an approximate medium; and emulsions.

Formulations suitable for parenteral administration include aqueous and non-aqueous isotonic sterile solutions, which contain buffers, antioxidants and preservatives. The formulations maybe in unit dose or multi-dose sealed contains.

Dosage amount and interval may be adjusted individually to provide plasma levels of the active moiety which are sufficient to maintain the antidiabetic and other favorable metabolic effects.

Alternatively, one may administer the compound in a local, rather than oral manner, for example, via injection of the compound directly into the target site, often in a depot or sustained release formulation.

A variety of delivery systems for the pharmacological compounds may be employed, including, but not limited to, liposomes and emulsions. The pharmaceutical compositions also may comprise suitable solid or gel phase carriers or excipients. Example of such carriers or excipients include, but are not limited to, calcium carbonate, calcium phosphate, various sugars, starches, cellulose derivatives, gelatin, and polymers such as polyethylene glycols.

In cases of local administration or selective uptake, the effective local concentration of the nutraceutical compound may be related to plasma concentration.

The invention accordingly comprises the several steps and the relation of one or more of such steps with respect to each of the others, and the product embodying properties, which are adapted to effect such steps and methods, all as exemplified in the following detailed disclosure, and the scope of the invention will be indicated in the claims.

A large number of cellular components and secondary metabolites derived from mushrooms, have been shown to affect the immune system and used in a variety of disease states. Mushrooms have been used as adaptogens and immunostimulants. An adaptogen as defined herein, is any substance that meets specific criteria for the category of plant derived biological response modifier, that may modify the host's biological response by a stimulation of the immune system. The principal component of these biological response modifiers is (1→3)—β-D-glucans. β-D-glucan, a polysaccharide isolated from mushrooms binds to lymphocyte surfaces or serum specific proteins, which activate macrophage, T-helper, natural killer cells and other effector cells. These increase the production of antibodies as well as interleukins (IL-1, IL-2) and interferon (IFN-r) which are released upon activation of effector cells. The carcinostatic effect of antitumor polysaccharides thus results from the activation of the host's immune system.

In addition to water-soluble β-D-glucans, mushrooms also contain β-D-glucans with heterosaccharide chains of xylose, mannose, galactose, and uronic acid, and β-D-glucan-protein complexes. The higher Basidiomycetes edible composition obtained grown in submerged culture in the present invention comprised of cellular and secondary metabolites, polysaccharides and specifically 1, 3-linked glucuronoxylomannan, and exhibit immunomodulatory and carcinostatic properties.

The higher Basidiomycetes mushrooms contain dietary fibers belonging to glucans, chitin, and heteropolysaccharides including, but not limited to, pectinous substances, hemi-celluloses or polyuronides. The β-glucans and chitinous substances are present primarily in the dietary fiber of mushrooms. Their carcinostatic activity has been attributed to their physicochemical interactions with hazardous materials such as carcinogenic substances, thereby preventing their absorption into the intestine and hastening their excretion. The higher Basidiomycetes edible compositions of the present invention comprise of dietary fibers belonging to β-glucans, chitin and heteropolysaccharides, having carcinostatic activity.

The effect of *T. mesenterica* submerged mycelium can be studied in the streptozotocin-induced type I diabetes model in Sprague Dawley male rats as described by G. S. Mahdi et al. Ann. Nutr. Metab 35: 65 (1991). Plasma glucose concentrations are measured seven days after a single does of streptozotocin in rats maintained on a casein based diet or a diet in which *T. mesenterica* replaces the protein supplied diet in which by casein in the control group. The rats maintained of the *T. mesenterica* diet generally regulate the glucose levels better than the casein fed group suggesting a hypoglycemic role for the nutriceuticals present in *T. mesenterica*.

The present invention is not to be limited in scope by the embodiments disclosed in the examples which are intended as an illustration of one aspect of the invention and any methods which are functionally equivalent are within the scope of the invention. Indeed, various modifications of the invention in addition to those shown and described herein will become apparent to those skilled in the art from the foregoing description. Such modifications are intended to fall within the scope of the appended claims.

Various publications are cited herein, the disclosures of which are incorporated by reference in their entireties.

It will thus be seen that the objects set forth above, among those made apparent from the preceding description, are efficiently attained and, since certain changes may be made in carrying out the above method and in the compositions set forth without departing from the spirit and scope of the invention, it is intended that all matter contained in the above description and shown in the accompanying figures shall be interpreted as illustrative and not in a limiting sense.

It is also to be understood that the following claims are intended to cover all of the generic and specific features of the invention herein described and all statements of the scope of the invention which, as a matter of language, might be said to fall there between.

What is claimed is:

1. A process for producing a one cell biomass rich in essential amino acids and polysaccharides of edible Basidiomycetes fungi *Tremella mesenterica* deposited under the Budapest Treaty with Centraalbureau voor Schimmelcultures (CBS) as Acc. No. CBS 101939, said process comprising:

cultivating the fungi *Tremella mesenterica* deposited under the Budapest Treaty with Centraalbureau voor Schimmelcultures (CBS) as Acc. No. CBS 101939 in submerged culture on nutrient media, and isolating the resulting biomass of edible fungi from the culture broth by alcohol precipitation.

2. The process for producing a biomass rich in essential amino acids and polysaccharides of edible Basidiomycetes fungi according to claim 1, wherein the CBS 101939 is precipitated by alcohol, and wherein CBS 101939 comprises glucuronoxylomannan producer cells of *Tremella mesenterica*, glucuronic acid, xylose or mannose.

* * * * *